(12) United States Patent
Buchalla et al.

(10) Patent No.: US 6,769,911 B2
(45) Date of Patent: Aug. 3, 2004

(54) LUMINESCENCE ASSISTED CARIES EXCAVATION

(75) Inventors: Wolfgang Buchalla, Indianapolis, IN (US); Aine M. Lennon, Indianapolis, IN (US)

(73) Assignee: Advanced Research & Technology Institue, Bloomington, IN (US)

( * ) Notice: Subject to any disclaimer, the term of this patent is extended or adjusted under 35 U.S.C. 154(b) by 57 days.

(21) Appl. No.: 09/835,673

(22) Filed: Apr. 16, 2001

(65) Prior Publication Data

US 2003/0022126 A1 Jan. 30, 2003

(51) Int. Cl.[7] .............................. A61C 3/00; A61C 5/00
(52) U.S. Cl. ........................................ 433/29; 433/215
(58) Field of Search .................................. 433/29, 215

(56) References Cited

U.S. PATENT DOCUMENTS

| | | | | |
|---|---|---|---|---|
| 4,290,433 A | | 9/1981 | Alfano | 352/318 |
| 4,479,499 A | | 10/1984 | Alfano | 433/29 |
| 4,498,868 A | * | 2/1985 | Schuss | 433/29 |
| 4,515,476 A | | 5/1985 | Ingmar | 356/318 |
| 4,642,738 A | * | 2/1987 | Meller | 433/29 |

(List continued on next page.)

FOREIGN PATENT DOCUMENTS

| | | |
|---|---|---|
| DE | 40 09 438 | 9/1991 |
| EP | 0 326 497 A2 | 8/1989 |
| EP | 0113152 * | 7/1994 |

OTHER PUBLICATIONS

Caries Research 1998:32:219–226, *Autofluorescence and Minteral Content of Carious Dentine: Scanning Optical and Backscattered Electron Microscopic Studies*, Avijit Banerjee, Alan Boyde, 1998 S. Karger AG Basel.

Caries Research 1996;30:93–99, *The Influence of Mineral Loss on the Auto–Fluorescent Behavior of in vitro Demineralised Dentine*, M.. H. van der Veen, J.J. Ten Bosch, 1996 S. Karger AG, Basel.

Web Page, www.kavousa.com—DIAGNOdent, Kaveo DiagnoDent.

Caries Research 2000:34:144–150, *In vitro Evaluation of Five Alternative Methods of Carious Dentine Excavation*, A. Banerjee, E.A.M. Kidd, T.F. Watson, 2000 S. Karger AG Basel.

British Dental Journal vol. 188, No. 9, May 13, 2000, *Dentine caries excavation: a review of current clinical techniques*, a. Banergee, T.F. Watson, E.A.M. Kidd.

Primary Examiner—John J Wilson
(74) Attorney, Agent, or Firm—Baker & Daniels (57) ABSTRACT

The present invention provides an improved method and apparatus for detecting dental caries (including residual caries) during treatment thereof. A dental handpiece in accordance with the present invention includes both an integral drill head (or other apparatus for excavating caries) and an integral light source operable to cause tooth luminescence. The light source is configured whereby tooth luminescence is caused when the dental handpiece is placed in operable position to treat the tooth with the drill head. During treatment, an observer can differentiate carious tooth substance from non-carious tooth substance due to the luminescent characteristics of each. Specifically, it has been found that when illuminated with a blue-violet light, the carious region of a tooth will appear as a red-orange central region surrounded by an intensely luminescent region of green color. The aforementioned intensely luminescent region is positioned intermediate the red-orange central region and a dark outer ring. According to the method of the present invention, the red-orange centered region is identified as the bacterially invaded zone of the carious lesion and is removed.

28 Claims, 5 Drawing Sheets

U.S. PATENT DOCUMENTS

| | | | |
|---|---|---|---|
| 5,306,144 A | 4/1994 | Hibst et al. | 433/29 |
| 5,382,163 A | 1/1995 | Putnam | 433/29 |
| 5,570,182 A | 10/1996 | Nathel et al. | 356/345 |
| 5,818,587 A | 10/1998 | Devaraj et al. | 356/349 |
| 5,894,620 A * | 4/1999 | Polaert et al. | 433/29 |
| 5,961,327 A | 10/1999 | Löhn | 433/80 |
| 6,024,562 A | 2/2000 | Hibst et al. | 433/29 |
| 6,053,731 A | 4/2000 | Heckenberger | 433/29 |
| 6,095,810 A * | 8/2000 | Bianchetti | 433/29 |
| 6,102,704 A | 8/2000 | Eibofner et al. | 433/215 |
| 6,135,774 A | 10/2000 | Hack et al. | 433/215 |

* cited by examiner

LUMINESCENCE ASSISTED CARIES EXCAVATION

BACKGROUND OF THE INVENTION

1. Field of the Invention

The present invention relates to a method and apparatus for facilitating the removal of substantially all the bacterially invaded tooth substance in a carious region, e.g., prior to placing a restoration in an affected area (i.e., enamel and dentin) of a tooth. More particularly, the present invention relates to an improved method and apparatus for the luminescent detection of the bacterially invaded tooth substance in a carious region during removal thereof to facilitate removal of substantially all of the bacterially invaded tooth substance, while providing maximum preservation of healthy tooth structure.

2. Description of the Related Art

To effect caries excavation, e.g., prior to positioning a restoration, the dentist must differentiate between carious tooth substance which will be removed and sound tooth substance which will be conserved. Currently several methods of differentiating between carious and non-carious tooth substance are available.

One available method utilizes the hardness differential between carious and non-carious tooth substance. A sharp dental explorer is utilized to probe the tooth substance and to determine if the tissue is soft or hard. Generally the soft tissue is thought to be carious, while the hard tissue is considered to be non-carious. Utilizing this technique is relatively time consuming to implement. Furthermore, this process is inaccurate (due, e.g., to the subjective analysis employed) and can therefore lead to removal of healthy (i.e., non-carious) tooth substance and can also lead to carious substance being overlooked. Additionally, probing the dentin region of the tooth close to the pulp chamber can disadvantageously lead to exposure of the pulp chamber.

Chemomechanical techniques have also been utilized to effect caries removal. Chemomechanical caries removal is effected by first mixing an appropriate compound, i.e., a compound which softens carious tooth substance. After mixing, the compound is emptied into a suitable instrument for application to the affected area of the tooth. Alternatively, the compound could be directly applied to the tooth after mixing. The carious dentin must be thickly covered with the compound and the compound must be left in place for a period of time (e.g., thirty seconds). An instrument is thereafter utilized to scrape out the softened tooth substance. The cavity is wiped clean and caries removal is checked with a probe. The steps of applying the compound and scraping away the softened tooth substance are repeated until the relevant tooth surface feels hard when probed. Finally, the cavity formed by this process may need to be adjusted with a hand or rotating instrument before a restoration may be placed. Clearly, chemomechanical caries removal is relatively time consuming and involves evaluation of caries removal using a sharp probe. As indicated above, differentiation between carious and non-carious tooth substance using a sharp probe is a subjective procedure which can produce inaccurate evaluations, therefore, the dentist may cease applying the operable compound with residual caries remaining.

A further method for distinguishing between carious and non-carious tooth substance during excavation utilizes a dye to facilitate visual differentiation between carious and non-carious tooth substance. In this technique, a dye which colors carious tooth substance, but not sound tooth substance is applied to a tooth which has been dried by compressed air. Since only the external surface of the tooth will be dyed, continuous re-application of the dye is necessary. Furthermore, dyes have been found to inaccurately color non-carious tooth substance, leading to unnecessary removal of sound tooth substance.

Problematically, the above-identified techniques for differentiating between carious and non-carious tooth substance while effecting caries removal, (e.g., to prepare a tooth to receive a restoration) are cumbersome, time consuming, and generally either do not provide for removal of substantially all of the carious tooth substance at an affected site, or may lead to removal of non-carious tooth substance. If all of the carious material is not removed, the bacteria and carious material that remain (i.e., residual caries) can become recurrent caries.

It is known to utilize fluorescence to differentiate between carious and non-carious tooth substance in a laboratory setting. A histological slice of an extracted tooth is made so that tooth fluorescence can be evaluated under a microscope. Furthermore, it is known to evaluate the fluorescence of teeth to identify early caries from outside a tooth utilizing a computational device to evaluate tooth fluorescence in an attempt to evaluate the presence or absence of caries in a tooth. In one known device, a laser diode provides pulsed light to be directed onto the tooth. Fluorescent light stimulated by the light provided by the laser diode is translated through a handpiece for evaluation by a computational device. The computational device is connected to a display utilized to indicate a numerical output based on the emitted fluorescent light.

Additionally, visual inspection of tooth fluorescence in the red region of the spectrum has been proposed to detect early stage caries. This visual detection has been utilized in conjunction with a laser treatment device to remove early stage caries in tooth enamel. This known device utilizes a cutoff wavelength of 620 nm in evaluating tooth fluorescence so that the early stage caries are displayed as bright spots in the red region of the visible spectrum. This known device utilizes an excitation radiation in the spectral range of 360 to 580 nm to cause tooth fluorescence. To effect treatment of early stage caries in tooth enamel, the intensity of radiation of the emitted light (utilized to cause tooth fluorescence) is increased to a sufficiently strong intensity to cause the early stage caries to die out.

Furthermore, attempts have been made to utilize visual inspection of tooth fluorescence for the detection of caries during treatment (i.e., drilling) of a tooth. In procedures of this type, a discrete light source (e.g., an argon laser) is utilized to direct a luminous beam at a tooth during treatment (i.e., drilling) of the tooth. Procedures of this type are difficult to implement because two discrete devices (i.e., the drill and the light source) must be concurrently placed in or near the mouth during treatment. In an effort to simplify use of these devices, a fiber optic lead is sometimes attached to the light source, and a clip is utilized to selectively affix the fiber optic lead to the dental handpiece containing the drill. This arrangement does not overcome the deficiencies of this device, as the dentist must still manipulate two devices (i.e., the laser, and the drill) and, problematically, the connections (e.g., power cords) of these devices may become tangled during treatment. Additionally, the discrete light source of this device is not well balanced and, to the contrary, is relatively weighty at the rear of the device. Therefore this device (i.e., the light source) cannot easily be balanced in the hand nor can this device be manipulated with any degree of precision. The method of caries removal utilized with this device indicates that caries will appear dark during fluorescence of tooth substance and that excavation of the dark areas of a fluorescent tooth should be removed to effect caries removal.

What is needed in the art is an apparatus and method for utilizing visual inspection of the luminescence of the substance of a tooth (e.g., enamel and dentin) during caries removal to facilitate accurate removal of substantially all of the bacterially invaded tooth substance in a carious region during the preparation of a tooth, e.g., for placing a restoration, which apparatus and method is relatively easy to implement.

What is further needed in the art is a method for identifying bacterially invaded tooth substance in a carious region via visual inspection of the luminescence of tooth substance, which method provides a more accurate indication of the bacterially invaded tooth substance in a carious region so that sound tooth substance can be preserved during caries excavation.

SUMMARY OF THE INVENTION

The present invention overcomes the above-identified disadvantages of the prior art by providing a dental handpiece housing a light source operable to cause tooth luminescence. The housing of the dental handpiece of the current invention contains both a mechanism for excavating caries (e.g., caries occupying portions of the enamel, the dentin, and the cementum layers of a tooth) as well as a light source and a light guide which directs light operable to cause luminescence of tooth substance (i.e., carious and non-carious tooth substance) onto an area of a tooth to be treated with the mechanism for excavating caries (e.g., a drill head, i.e., the operable end of an oscillating or rotating drill bit utilized to effect caries excavation). In one exemplary embodiment, the light source produces light having a wavelength at or below the lower end of the visible range of the spectrum (e.g., in the blue-violet portion of the visible spectrum). A filter is utilized to allow the dentist to better evaluate the tooth luminescence to determine the presence or absence of caries, as further described below. The present invention overcomes many shortcomings of the prior art by advantageously combining a mechanism for excavating caries with a light source operable to produce tooth luminescence into a single instrument. Furthermore, the method of the present invention provides a more accurate method for determining the presence or absence of caries via tooth luminescence.

According to the method of the present invention, light having a wavelength operable to produce luminescence in tooth substance (e.g., light having a wavelength toward the lower end of the visual spectrum, e.g., in the blue-violet region of the visible spectrum) is projected onto an affected tooth. In one exemplary embodiment, a filter having a cutoff wavelength at the lower end of the green region of the visual spectrum is then utilized to inspect the illuminated area. The carious lesion appears as multiple regions of different colors, including a bright orange-red central region surrounded by an intensely luminescent area appearing green in color and a dark outer ring. According to the method of the present invention, the bright orange-red central region is identified as the bacterially invaded region. The region outside the dark outer ring comprises unaffected tooth substance (e.g., enamel and dentin). The intensely luminescent zone (green in color) intermediate the red-orange central area (i.e., the carious lesion) and the dark outer ring is much brighter than the normal dentin outside the dark outer ring. The central red-orange zone comprises bacterially invaded tooth substance which should be removed, however, the intensely luminescent zone intermediate the dark red-orange central area and the dark outer ring should not be removed. Known methods of utilizing fluorescence of tooth substance to determine carious regions (while treating, i.e., drilling the caries) indicate that dark areas of fluorescent tooth substance should be recognized as carious material and should be removed. Removal techniques of this type would indicate removal to the dark outer ring identified by the present invention, and, therefore, lead to unnecessary removal of non-bacterially invaded tooth substance. With the method of the present invention, a dentist may accurately discern (via visible luminescence) bacterially invaded tooth substance during removal thereof so that healthy tooth substance can be efficiently preserved.

The invention, in one form thereof, comprises a dental handpiece having a housing with a drill head protruding from the housing. The drill head is operably connected to a motor mounted in the housing. A light source is also mounted in the housing and is operable to produce light through an opening in the housing. The opening in the housing is located so that the light produced by the light source is projected substantially in a direction along which the drill head protrudes from the housing. The light has a desired wavelength operable to produce tooth luminescence.

The invention, in another form thereof, comprises a dental handpiece having a housing with excavation means for excavating carious material occupying a portion of a tooth. The dental handpiece further includes illumination means for emitting light of a desired wavelength operable to produce tooth luminescence. The illumination means is mounted in the handpiece housing together with the excavation means. Guide means are utilized to guide an emitted light from the illumination means to an opening in the housing. The opening is located in the housing so that the emitted light is projected onto the tooth when the excavation means is operably positioned for excavating the bacterially invaded region of the tooth.

The apparatus of the present invention may further include filter means for filtering a luminescence of the tooth caused by the light produced by the light source in the dental handpiece. In this form of the current invention, the filter means has a cutoff wavelength whereby the light produced by the light source cannot traverse the filter means. Generally, the filter means only allows light having wavelength between the red and the green region of the visible spectrum to pass. In one exemplary embodiment, the filter has a cutoff wavelength of 500 nm, whereby only light having a wavelength equal to or greater than 500 nm can traverse the filter means. The filter means utilized in accordance with the present invention can include, e.g., colored glass filters, coated glass filters, or mirrors (i.e., dichroic mirrors).

The invention, in another form thereof, comprises a method of identifying a caries in a tooth. The method of this form of the current invention comprises the steps of: projecting a light of desired wavelengths onto the tooth, the light causing a luminescence of the tooth; observing the luminescence of the tooth; identifying a red-orange central region surrounded by an intensely luminescent region and a dark outer ring, whereby the intensely luminescent region is intermediate the red-orange central region and the dark outer ring; and recognizing the red-orange central region as a bacterially invaded region.

An advantage of the present invention is the ability to accurately remove substantially all of the bacterially invaded tooth substance during preparation of a tooth, e.g., to receive a restoration, while avoiding removal of non-bacterially invaded tooth tissue.

Another advantage of the present invention is the provision of a relatively non-cumbersome method and apparatus for effecting removal of substantially all of the bacterially invaded tooth substance at an affected site of a tooth.

Yet another advantage is the ability to decrease the time necessary to effect removal of carious tooth substance relative to conventional techniques. The method of the current invention is relatively efficient compared to conventional techniques because time-consuming changes of instruments and/or concurrent use of multiple instruments, as well as application and re-application of dye is avoided.

BRIEF DESCRIPTION OF THE DRAWINGS

The above-mentioned and other features and advantages of this invention, and the manner of attaining them, will become more apparent and the invention itself will be better understood by reference to the following description of an embodiment of the invention taken in conjunction with the accompanying drawings, wherein.

Corresponding reference characters indicate corresponding parts throughout the several views. Although the drawings represent embodiments of the present invention, the drawings are not necessarily to scale and certain features may be exaggerated to better illustrate and explain the present invention. The exemplifications set out herein illustrate exemplary embodiments of the invention, and such exemplifications are not to be construed as limiting the scope of the invention in any manner.

DETAILED DESCRIPTION OF THE INVENTION

Figures 1, 2:
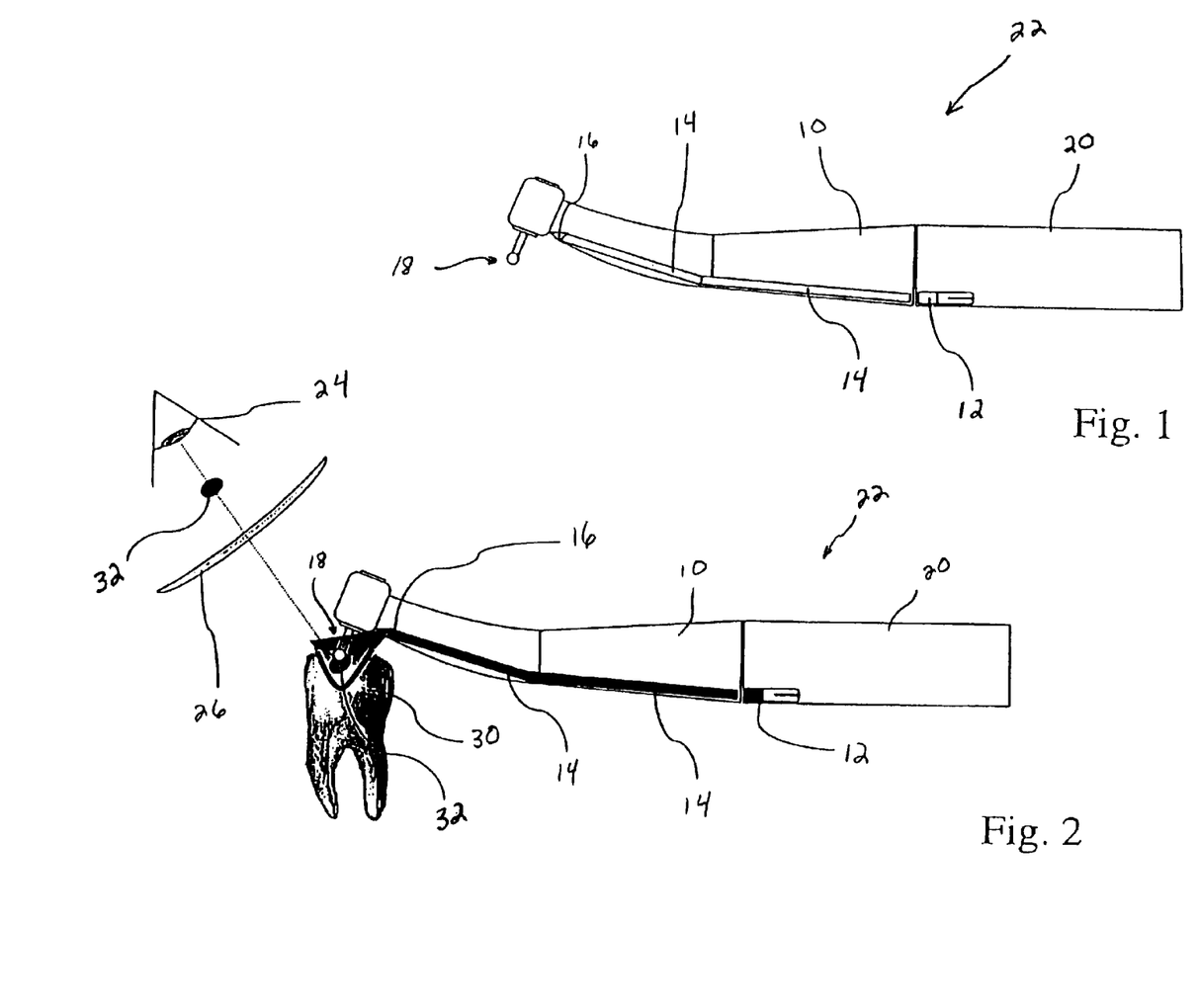
FIG. 1 is a plan view of a dental handpiece in accordance with the present invention.
FIG. 2 is a plan view illustrating application of a dental handpiece in accordance with the present invention to the affected site of a tooth.

Referring now to the drawings and particularly to FIG. 1, dental handpiece 22 includes housing 10, with motor housing 20 having a motor (not shown) contained therein. In an alternative embodiment, housing 10 does not contain a motor, but rather includes an air turbine located adjacent drill head 18 (discussed hereinbelow). Dental handpiece 22 further includes light source 12. As illustrated, light source 12 is contained within motor housing 20, although it is contemplated that light source 12 may be positioned in various alternative locations within housing 10. Light source 12 is connected via light guides 14 to opening 16 in housing 10. Dental handpiece 22 further includes drill head 18 (or other device for excavating unhealthy tooth substance) operably connected to the motor housed within motor housing 20. Dental handpiece 22 is connected to appropriate sources of power as is conventional in the art. Opening 16 is configured whereby light produced by light source 12 is projected from dental handpiece 22 substantially in a direction along which drill head 18 protrudes from dental handpiece 22.

FIG. 2 illustrates application of dental handpiece 22 to tooth 30 to effect treatment of carious region 32. As illustrated in FIG. 2, light source 12 is activated to produce a light following light guides 14 to opening 16. A lens or other appropriate device may be utilized to guide the light produced by light source 12 as it exits opening 16. In use, light produced by light source 12 is applied to tooth 30 to cause luminescence thereof. Observer 24 can then evaluate the luminescence of tooth 30 to determine the location of bacterially invaded region 32. As illustrated in FIG. 2, filter 26 is positioned intermediate observer 24 and tooth 30. Filter 26 is operable to facilitate evaluation of tooth luminescence to determine the location of bacterially invaded region 32 as is further described hereinbelow.

Figure 3:
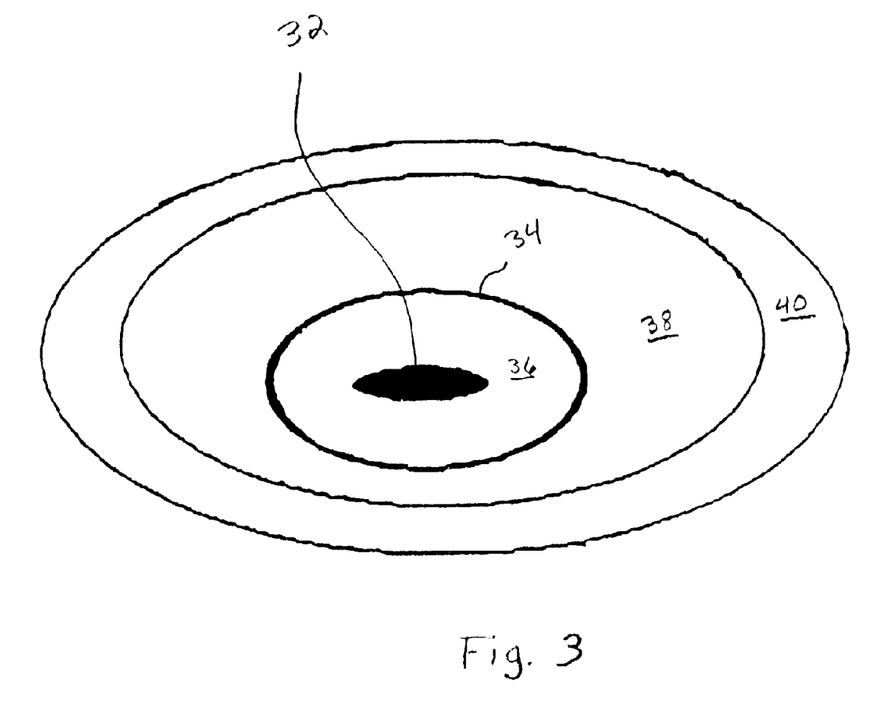
FIG. 3 is a schematic depiction of the luminescence of a tooth including a carious lesion.

FIG. 3 illustrates in diagrammatic form the luminescent region of tooth 30. As illustrated in FIG. 3, luminescence of tooth 30 is observed to include red-orange central region 32 surrounded by intensely luminescent region 36 (appearing green in color) and dark outer ring 34. Intensely luminescent region 36 is positioned intermediate outer ring 34 and red-orange central region 32. Dentin 38 and enamel 40 are seen to have luminescence of decreasing intensity, that is, dentin 38 has a higher intensity of luminescence than enamel 40. Furthermore, the luminescence of intensely luminescent region 36 is greater than the luminescence of dentin 38. Upon recognizing the red-orange central region 32 and dark outer ring 34, as well as luminescent regions 36, 38, and 40 (having decreasing luminescent intensity), observer 24 can readily recognize red-orange central region 32 and, according to the present invention, identify red-orange central region 32 as the bacterially invaded region. Drill head 18 may subsequently be applied to red-orange central region 32 to effect removal thereof Advantageously, a dentist may continually observe and evaluate bacterially invaded region 32 while applying drill head 18 for removal thereof.

Outer ring 34 is seen to be the translucent zone as described histologically. This hypermineralized area forms when the lumen of the dentinal tubules ahead of the advancing front of the carious lesion fill with mineral. Intensely luminescent region 36 is seen to correspond with the demineralized zone, since increased fluorescent radiance in demineralized dentin is recognized. It has been suggested that the fluorescence of the fluorophore in dentin is quenched when it is linked to hydroxyapatite, and that demineralization of dentin leads to de-quenching. Therefore, outer ring 34 appears dark, as more hydroxyapatite is present and quenching occurs, while intensely fluorescent region 36 appears brighter as a result of de-quenching. In red-orange central region 32, bacteria has invaded the tooth. Oral microorganisms are known to produce red fluorescence and, for this reason, the bacterially invaded zone appears red-orange.

Conventionally, tooth substance would be excavated to outer ring 34. The identifying mechanism of the present invention advantageously allows for accurate recognition of bacterially invaded region 32 of tooth 30 so that bacterially invaded region 32 may be removed while efficiently retaining the non-bacterially invaded tooth substance of tooth 30. Furthermore, the technique of the current invention will allow for identification of various bacterially invaded regions of calcified tissue.

In an alternative embodiment, a video camera can be attached to or integrated with dental handpiece 22. For example, a CCD (charged coupled device) camera may be utilized as a photosensitive element within dental handpiece 22. In an embodiment utilizing a video camera, an enlarged image of the working area could be displayed on a monitor and the dentist and the patient could view the displayed image during treatment. Furthermore, the image produced by the method of the current invention could be displayed in false colors on the monitor so that the carious region could be more easily recognized.

Figure 4:
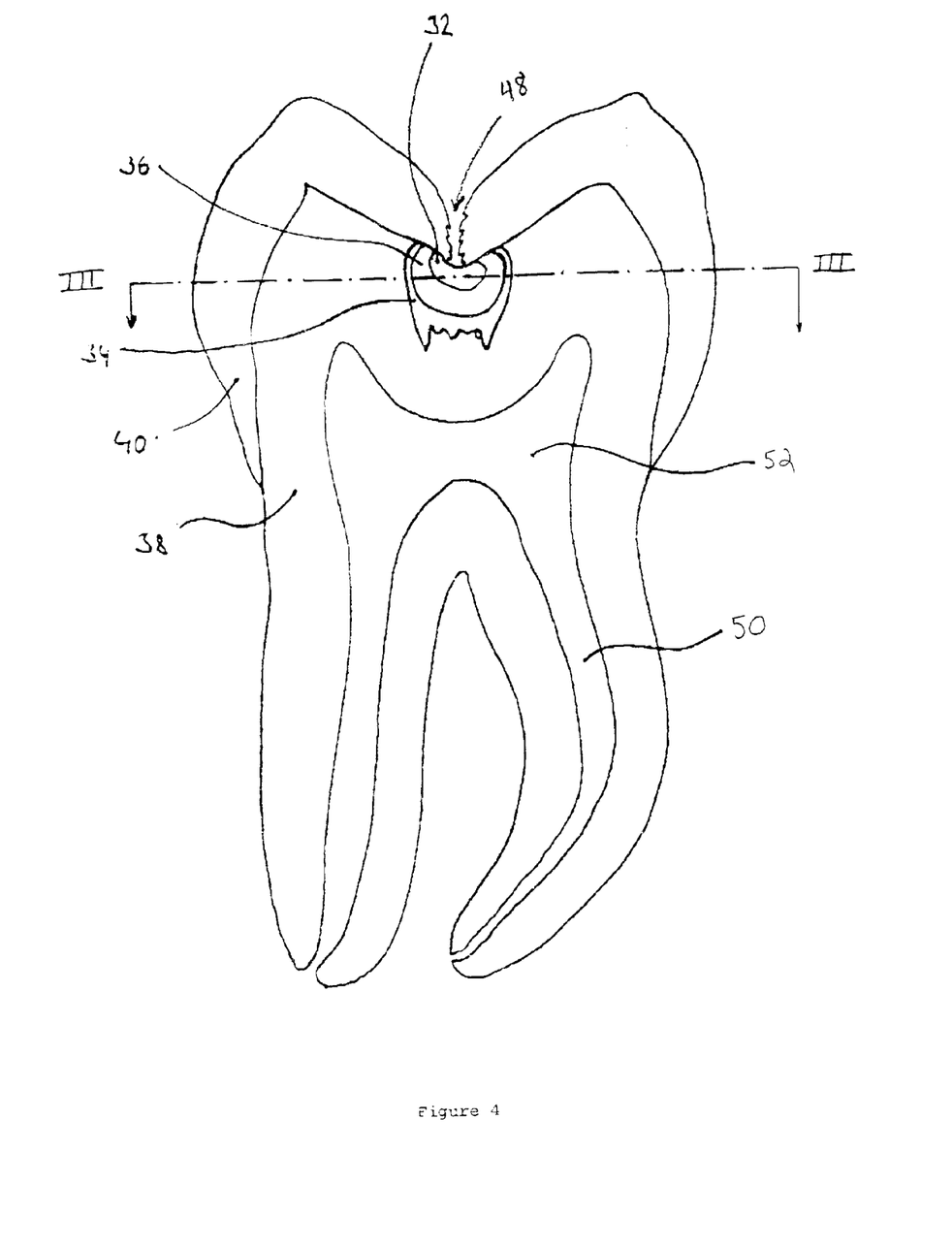
FIG. 4 is a longitudinal section through a molar having a carious lesion.

The various regions identified in FIG. 3 will, in use, be identifiable to varying degrees, since portions of these regions will be obstructed by tooth substance (e.g., enamel). As illustrated in FIG. 4, portions of bacterially invaded region 32 can be viewed directly through cavity 48. As cavity 48 is enlarged to effect removal of carious region 32, greater portions of carious region 32 will be directly viewable through cavity 48. If cavity 48 is expanded beyond carious region 32, intensely luminescent region 36 will be immediately discernible through cavity 48 and excavation will be discontinued as intensely luminescent region 36 is encountered. As illustrated in FIG. 4, the schematic depiction of FIG. 3 corresponds to a cross section of the tooth illustrated in FIG. 4, taken along line III—III.

It is further contemplated that an apparatus in accordance with the present invention will facilitate removal of plaque and calculus. Plaque and calculus both produce red luminescence. These luminescent red regions can, advantageously, be easily removed utilizing an integrated device in accordance with the current invention having both a light source with an emission spectrum operable to produce luminescence of tooth substance (both healthy and non-healthy tooth substance) as well as an instrument operable to remove plaque and calculus, e.g., a scraping device, or rotating brush.

The device of the current invention may also be utilized to more easily remove filling material. Many times, tooth colored filling material is utilized in modem dentistry. In situations where tooth colored filling material must be removed, it can be difficult to discern the transition from the filling material to the healthy tooth. Tooth colored filling materials will fluoresce differently from tooth substance and, therefore, the device of the present invention may advantageously be utilized to remove such substance. Furthermore, the apparatus of the current invention may advantageously be utilized to remove an amalgam filling for replacement. Many times, the dentin underlying an amalgam filling is darkly stained due to silver ions which penetrate out from the amalgam into the tissue. These dark areas can inhibit the detection of caries in white light, since it will be difficult to discern the caries (which can appear as a brown or discolored area under white light), from the discolored area caused by the amalgam filling. The apparatus and method of the current invention will therefore advantageously facilitate caries identification in situations in which dentin has been stained by an amalgam filling, as the caries will appear red-orange, as described above.

It is further contemplated that the instrument of the current invention may advantageously be utilized during the removal of an impacted or retained tooth or tooth germ. The tooth or tooth germ will strongly fluoresce while the bone in which it is impacted will not. Therefore, an instrument in accordance with the present invention may advantageously be utilized during removal of an impacted or retained tooth or tooth germ. Yet another application of the apparatus of the current invention is in the removal of broken roots remaining in the jaw after a tooth has been extracted. Such roots remain in the bone and the dentist typically must remove bone to reach the roots and remove them. Since the root will fluoresce differently than the bone in which it is contained, the apparatus of the current invention may advantageously be utilized to remove such broken roots while efficiently maintaining bone stock.

The apparatus of the current invention is further useful in endodontics. Specifically, prior to root canal treatment, the root canal can be difficult to find. Conventionally, tooth substance is drilled away until the root canal can be found. Root canal 50 is illustrated, e.g., in FIG. 4. With the apparatus and method of the current invention, pulp chamber 52 (FIG. 4) does not fluoresce green and can, therefore, be seen through the green luminescence of the dentin structure. After determining the location of pup chamber 52, root canal 50 is easily found, without unnecessary loss of healthy tooth substance. Identification of the pulp chamber is further useful when excavating a cavity, since, during cavity excavation, the dentist does not want to excavate into pulp chamber 52 (FIG. 4). Furthermore, bacterially invaded pulp will appear red in color and therefore, according to the method of the present invention, it will be possible to determine bacterially invaded portions of the pulp chamber or root canal.

In one exemplary embodiment, filter 26 (FIG. 2) comprises an optical long pass filter having a cutoff wavelength of 500 nm (i.e., the lower-most wavelength in the green area of the visible spectrum). In another exemplary embodiment, filter 26 comprises a bandpass filter allowing wavelengths from 500 nm–780 nm to traverse filter 26. Typically, light source 12 will be operable to produce light having a wavelength of less than 500 nm (i.e., in or below the blue-violet region of the visible spectrum). The luminescence of dentin 38 will produce a yellow-green light, while central region 32 will appear a red or orange color, therefore, filter 26 will facilitate identification of the various portions of the carious region, as only visible light having wavelengths in the green, yellow, orange and red portions of the visible spectrum will traverse filter 26. Optical filter 26 may be incorporated into a pair of glasses, or a clip-on unit for use with existing eye glasses worn by observer 24. Furthermore, filter 26 may be incorporated into a disposable mask, or a shield to be held by a dental assistant.

Light source 12 may comprise, e.g., a filament lamp, or a semiconductor device (e.g., a laser diode or a light emitting diode). If a filament lamp is utilized, a filterglass bulb or other additional filter may be utilized to produce the desired wavelength, i.e., a wavelength at the lower end of the visible spectrum. Furthermore, an argon arc lamp may be utilized as light source 12. As stated supra, the desired wavelength is typically less than or equal to 500 nm, although any wavelength operable to produce tooth luminescence is acceptable. In one exemplary embodiment, light source 12 produces light having a wavelength of 405 nm. Discrete light sources may be retrofit into existing dental handpieces having a conventional light source (a light source inoperable to produce the desired/required tooth luminescence). Furthermore, an add-on filter may be utilized to produce the desired wavelength exiting opening 16 (FIGS. 1 and 2). If an add-on filter is utilized at opening 16, light source 12 may be a conventional white light source. In this way, a dental handpiece having a conventional light source may easily be retrofitted for use with the method of the current invention. Light guides 14 comprise, e.g., a glass rod assembly, or fiber optic bundle. If a filament lamp, or a lamp having a part of its emission spectrum outside the desired excitation spectrum is utilized as light source 12, light guides 14 may contain the appropriate optical filter to limit the light exiting opening 16 to the desired wavelength (discussed above). A filter (e.g., colored glass filters, coated glass filters, prisms, mirrors (i.e., dichroic mirrors), or gratings) can also be placed directly in front of light source 12, or otherwise in the light path generated by light source 12.

While the exemplary embodiment has been described as including drill head 18, it is contemplated that various mechanisms for excavating carious tooth material may be utilized including, e.g., various burs, drills, diamond tipped implements, or other known devices. These various mechanisms may be either rotating or oscillating. Furthermore, drill head 18 may be replaced with a sharp probe or sharp concave, spoon-like instrument for scrapping away non-healthy tooth substance, such as, e.g., plaque or calculus. Calculus removal may be effected in accordance with the present invention utilizing a hand instrument such as, e.g., a scaler, or a sonic or ultrasonic oscillating instrument. Furthermore, air abrasion may be utilized in accordance with the present invention. Conventionally, air abrasion is performed utilizing an air scaler where salt crystals are mixed with an air stream and are directed to the treatment area with the addition of water to prevent the distribution of dust. Furthermore, it is known to utilize air abrasion with silica particles to prepare a cavity. As is known in the art, air abrasion utilizing silica particles is utilized to prepare a cavity as opposed to removing calculus due to its relatively strong abrasive nature. Additionally, brush heads may be utilized for removal of plaque, stain, and calculus in accordance with the present invention.

The present invention further contemplates a device having both a white light source as well as a luminescence producing light source as described above. In such an embodiment, the white light illumination and the excitation illumination could be switched on and off alternatively so that the handpiece could be utilized both in a conventional manner and to effect the method of the present invention. Furthermore, a movable filter could be utilized in accordance with the present invention to be selectively positioned in the light path from a white light source so that the device will alternatively emit white light, or light having a desired excitation wavelength as described above. Alternatively, a liquid-crystal filter or other means known in the art may be used to switch between the desired wavelength areas without the necessity of moving parts.

STUDY

The following study of the method and apparatus of the current invention outlines the advantages of the current invention over several conventional methods.

The following abbreviations are used in this study:

TABLE I

Abbreviations

| Abbreviation | Complete Form |
|---|---|
| VL | Visible Luminescence as described supra and depicted in FIG. 3 |
| nm | Nanometer |
| μm | Micrometer |
| PLM | Polarized Light Microscopy |
| ppv | Positive Predictive Value |
| npv | Negative Predictive Value |
| Diag. | Diagnodent |
| Dye | Caries Detector Dye |
| VT | Visual Tactile Examination |

For the purposes of this study, detection of residual caries using VL indicates detection of the bacterially invaded region as described above.

1. Hypotheses

At the outset, the following two hypotheses were proffered.

1. If residual caries is present, it will be detectable using VL.
2. If no residual caries is detectable using VL, the cavity floor is caries-free.

2. Materials and Methods

Figure 5:
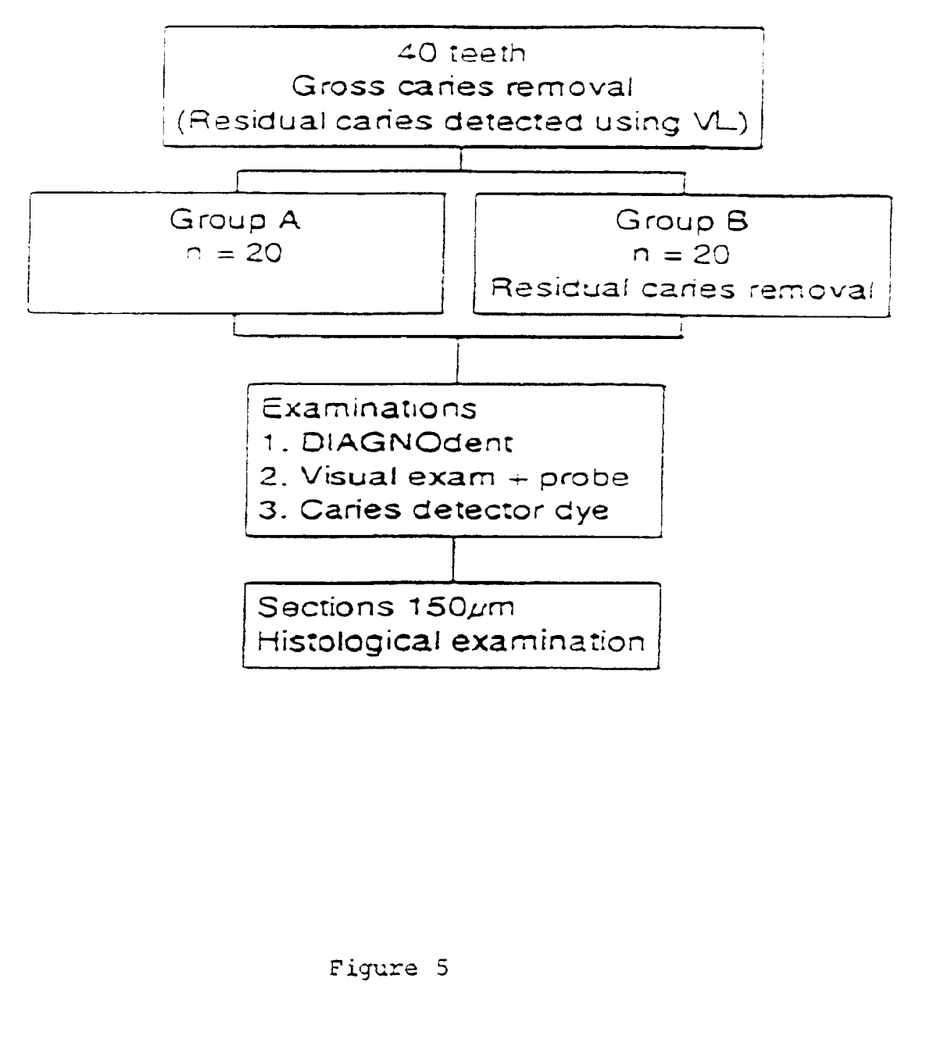
FIG. 5 is a table outlining the study of the method and apparatus of the current invention described below.

An outline of the study is provided in FIG. 5, and further described hereinbelow.

Sample Selection and Storage

Bitewing radiographs of extracted human teeth were made and used to select 40 teeth with $D_2$ and $D_3$ coronal caries. The selected teeth were stored in 0.01% thymol solution. Care was taken that the samples did not dry out at any time during the experiment.

Gross Caries Removal

Figure 6:
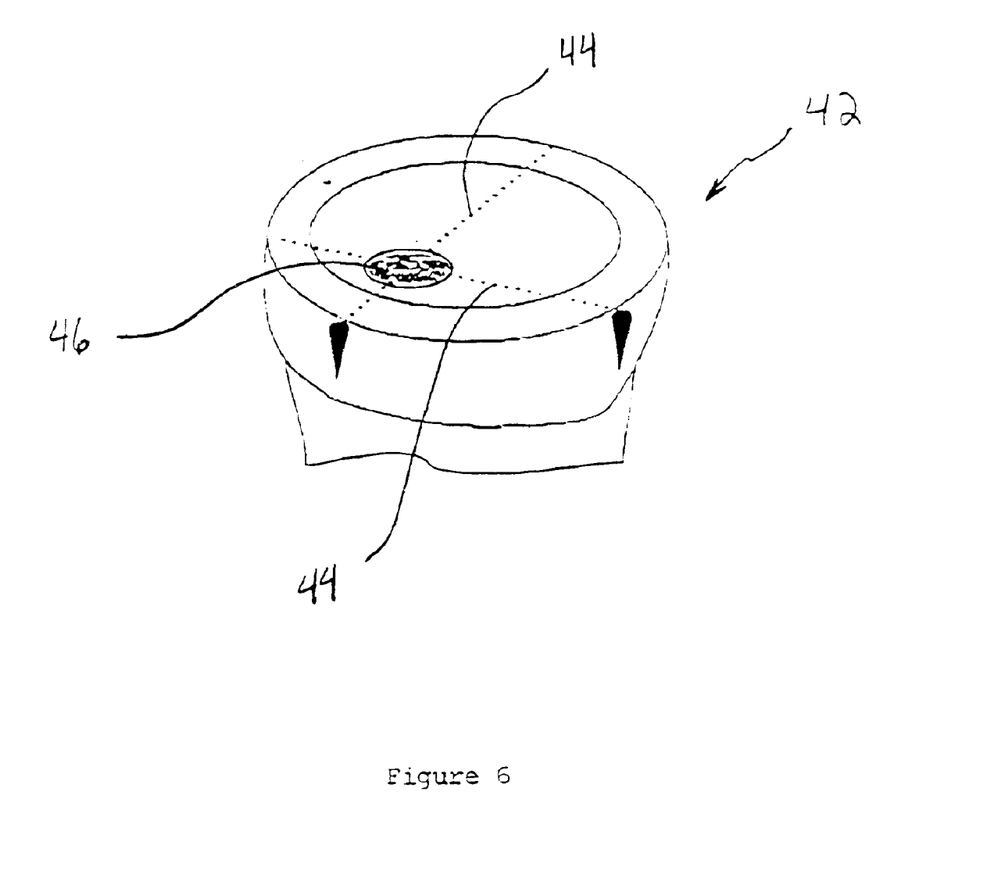
FIG. 6 is a partial perspective view of a tooth utilized in the study outlined below and illustrating marking of a carious lesion as described hereinbelow.

Gross caries was removed by grinding teeth perpendicularly to the carious surface using sandpaper (grit 600) under continuous water-cooling until enamel was removed and only a small amount of residual caries was detectable using VL. Specifically, the samples were illuminated with blue-violet light generated with an argon arc lamp and a band-pass filter with a band of 80 nm and a peak transmission at 370 nm. The samples were viewed through a filter (having a cutoff wavelength of 515 nm). The position of the lesion was then recorded in enamel using a permanent marker as shown in FIG. 6. Specifically, a permanent marker was utilized to form markings 44 on ground tooth 42. As illustrated, markings 44 are operable to identify the location of carious lesion 46.

Removal of Residual Caries

The teeth were then split randomly into two groups (A & B) of 20 teeth each. In group A, the teeth remained untreated. In group B the teeth were treated according to the method and apparatus of the current invention until no residual caries was detectable using VL.

Examination of Samples

All samples (n=40) were then examined for presence or absence of residual caries by a "blinded" examiner, using the techniques outlined below.

1. Laser fluorescence measurements were made for each sample using a DIAGNODENT device available from KaVo, Biberach, Germany. Specifically, a DIAGNODENT type no. 2095 was utilized. The DIAGNODENT device utilizes a laser to detect tooth fluorescence which is then conveyed to a computational device which displays a numerical output based upon the tooth fluorescence. The instrument was calibrated according to the manufacturer's instructions. The samples were dried briefly using compressed air, and the highest DIAGNODENT reading from the marked lesion area was recorded for each sample. The cutoff for sound tissue was set at 15.
2. For the visual tactile examination, the teeth were dried briefly using compressed air and were viewed under a conventional dental unit light. The examiner made a decision on the presence or absence of residual caries according to the color and hardness of the marked lesion area, with the aid of a sharp explorer.
3. Caries detector dye (i.e., Caries DetectorR) available from Kuraray, Japan was applied to the marked lesion area of each sample for 10 seconds and then rinsed with water. The examiner recorded the presence of residual caries when the marked lesion area was stained.

Thin Slice Preparation

Thin slices (150 μm) were prepared from each tooth perpendicularly to the surface cut during caries removal, through the center of the lesion using a hard tissue microtome available from SCIFAB, Lafayette, Colo., U.S.A. (i.e., Series 1000 Deluxe Hard Tissue Microtome).

Histology

Histological examinations were carried out to determine the presence or absence of residual caries using PLM. The thin sections were imbibed in Quinoline for 24 hours. The slices were then examined in transmitted light and between crossed polars at magnifications up to ×160. Presence or absence of the zone of bacterial invasion was recorded.

Statistical Methods

Sensitivity, specificity, ppv, npv, and % correct were computed for each method using PLM as the gold standard. Comparisons between the methods for differences in sensitivity, specificity, and % correct were made using multiple McNemar's tests for binary-paired data. No adjustments were made for multiple comparisons. Comparisons were considered statistically significant when the p-value was less than 0.05.

3. Results

Both of the stated hypotheses were proven: When residual caries is present it is detectable using VL (100% sensitivity). When no caries is detectable using VL the samples are caries free (100% npv).

The sensitivity, specificity, ppv, npv, and % correct for each method are given in Table 1 below. Sensitivity indicates that cavities excavated are caries free, while specificity indicates that caries detected by the particular method are true caries. Specifically, values of sensitivity, specificity, ppv, npv, and % correct are determined as follows:

% correct=the number of results where particular test method agrees with the gold standard/total number in sample;

Sensitivity=the number testing positive according to the particular test method (when the gold standard tests positive)/the number testing positive according to the gold standard;

Specificity=the number testing negative according to the particular method (when the gold standard tests negative)/over the number testing negative according to the gold standard;

ppv=the number testing positive according to the gold standard (when the method in question is positive)/the number testing positive according to the method in question; and npv=the number testing negative according to the gold standard (when the method in question is negative)/the number testing negative according to the method in question.

For example, % correct, specificity, sensitivity, npv, and ppv are computed for visual tactile examination (VT) as follows:

TABLE II

RESULTS

| Method | % Correct | | Specificity | | Sensitivity | | npv | | ppv | |
|---|---|---|---|---|---|---|---|---|---|---|
| | n | % | n | % | n | % | n | % | n | % |
| Diag | 40 | 85 | 22 | 77 | 18 | 94 | 18 | 94 | 22 | 77 |
| VT | 40 | 83 | 22 | 77 | 18 | 89 | 19 | 89 | 21 | 76 |
| Dye | 40 | 50 | 22 | 27 | 18 | 78 | 10 | 60 | 30 | 47 |
| VL | 40 | 95 | 22 | 91 | 18 | 100 | 20 | 100 | 20 | 90 |

% correct$_{VT}$ = 33/40 = 83%
Specificity$_{VT}$ = 17/22 = 77%
Sensitivity$_{VT}$ = 16/18 = 89%
npv$_{VT}$ = 17/19 = 89%
ppv$_{VT}$ = 16/21 = 76%

VL showed the greatest sensitivity, specificity, % correct, and predictive values of any of the methods tested. VL had significantly higher % correct (95%) than DIAGNODENT (85%) and caries detector dye (50%). Although the visual tactile method had a lower % correct (83%) than DIAGNODENT, this difference was statistically insignificant, but approaches the 0.05 cutoff of significance. VL had significantly higher sensitivity than caries detector dye. No other significant sensitivity differences were found between the methods. Results of the comparison between the methods are given in Table III. VL, visual tactile, and DIAGNODENT had significantly higher specificity than caries detector dye, but were not significantly different from each other.

TABLE III

| | p-values for comparisons between methods | | |
|---|---|---|---|
| | % Correct | Specificity | Sensitivity |
| Diag. vs. Dye | 0.0010 | 0.0023 | 0.1797 |
| Diag. vs. VL | 0.0455 | 0.0833 | 0.3173 |
| Diag. vs. VT | 0.7055 | 1.0000 | 0.5637 |
| Dye vs. VL | 0.0001 | 0.0005 | 0.0455 |
| Dye vs. VT | 0.0003 | 0.0009 | 0.1573 |
| VL vs. VT | 0.0588 | 0.1797 | 0.1573 |

The individual results for each method are given in Table IV below.

4. Conclusion

Visible luminescence showed the greatest sensitivity, specificity, % correct, and predictive values of any of the methods tested. It can be concluded that this method is an improvement over the currently available aids for residual caries detection outlined above.

TABLE IV

| | | Individual results | | | |
|---|---|---|---|---|---|
| ID | Group | Visual tactile | DIAGNO-DENT | DIAGNO-DENT ≧15 | Caries detector | PLM |
| 8 | a | y | 99 | y | y | y |
| 17 | a | y | 48 | y | n | y |
| 18 | a | y | 99 | y | y | y |
| 24 | a | y | 37 | y | y | y |
| 30 | a | y | 68 | y | y | y |
| 33 | a | y | 21 | y | y | y |
| 40 | a | y | 99 | y | y | y |
| 42 | a | y | 76 | y | y | y |
| 46 | a | y | 45 | y | y | y |
| 47 | a | y | 15 | y | y | n |
| 56 | a | y | 8 | n | y | y |
| 61 | a | y | 99 | y | y | y |
| 77 | a | y | 63 | y | y | y |
| 109 | a | n | 19 | y | n | n |
| 130 | a | n | 34 | y | n | y |
| 173 | a | y | 28 | y | n | y |
| 180 | a | n | 95 | y | n | y |
| 185 | a | y | 21 | y | y | y |
| 196 | a | y | 51 | y | y | y |
| 198 | a | y | 23 | y | y | y |
| 1 | b | n | 4 | n | n | n |
| 6 | b | y | 12 | n | y | n |
| 12 | b | n | 14 | n | y | n |
| 19 | b | y | 10 | n | y | n |
| 21 | b | n | 5 | n | y | n |
| 23 | b | y | 41 | y | y | n |
| 38 | b | n | 5 | n | n | n |
| 39 | b | n | 4 | n | y | n |
| 48 | b | n | 8 | n | y | n |
| 51 | b | n | 40 | y | y | n |
| 52 | b | y | 35 | y | y | n |
| 54 | b | n | 6 | n | y | n |
| 72 | b | n | 2 | n | y | n |

TABLE IV-continued

| | | | Individual results | | | |
|---|---|---|---|---|---|---|
| ID | Group | Visual tactile | DIAGNO-DENT | DIAGNO-DENT ≧15 | Caries detector | PLM |
| 73 | b | n | 6 | n | n | n |
| 79 | b | n | 7 | n | y | n |
| 82 | b | n | 11 | n | y | n |
| 87 | b | n | 6 | n | y | n |
| 91 | b | n | 2 | n | y | n |
| 102 | b | n | 6 | n | n | n |
| 123 | b | n | 8 | n | n | n |

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A dental handpiece comprising:

a housing;

a drill bit protruding from said housing, said drill bit operably connected to a motor mounted in said housing; and a light source mounted in said housing, said light source operable to produce a light through an opening in said housing, said opening being located in said housing such that said light produced by said light source is projected substantially in a direction along which said drill bit protrudes from said housing, said light having a desired wavelength operable to produce tooth luminescence for detection of a carious region of a tooth, whereby said drill bit is operable to excavate a portion of said carious region.

2. The dental handpiece of claim 1, further comprising:

a fiber optic bundle connecting said light source to said opening.

3. The dental handpiece of claim 1, further comprising:

a glass rod assembly connecting said light source to said opening.

4. The dental handpiece of claim 1, wherein said light produced by said light source has a wavelength in the blue-violet region of the visible spectrum.

5. The dental handpiece of claim 1, wherein said light produced by said light source has a wavelength of 405 nm.

6. The dental handpiece of claim 1, wherein said light source comprises a filament lamp having a filterglass bulb.

7. The dental handpiece of claim 1, wherein said light source comprises a semiconductor device.

8. A dental handpiece comprising:

a housing;

excavation means for excavating a portion of a carious material occupying a portion of a tooth;

illumination means for emitting a light of a desired wavelength operable to produce tooth luminescence for detection of said carious material, said illumination means mounted in said housing; and guide means for guiding an emitted light from said illumination means to an opening in said housing, said opening being located in said housing such that said emitted light is projected onto said tooth when said excavation means is operably positioned for excavating said portion of carious material.

9. The dental handpiece of claim 8, wherein said excavation means comprises a drill bit protruding from said housing and operably connected to a motor mounted in said housing.

10. The dental handpiece of claim 8, wherein said illumination means comprises a filament lamp with a filterglass bulb having a cutoff wavelength whereby said emitted light is in the blue-violet region of the spectrum.

11. The dental handpiece of claim 8, wherein said illumination means comprises a semiconductor device.

12. The dental handpiece of claim 11 where said emitted light has a wavelength of 405 nm.

13. A method of identifying a caries in a tooth, comprising:

projecting a light of a desired wavelength onto the tooth, said light causing a luminescence of the tooth;

observing the luminescence of the tooth;

identifying a red-orange central region surrounded by an intensely luminescent region and a dark outer ring, whereby the intensely luminescent region is intermediate the red-orange central region and the dark outer ring; and recognizing the red-orange central region as a bacterially invaded region.

14. The method of claim 13, wherein said intensely luminescent region intermediate the red-orange central region and the dark outer ring comprises a green region.

15. The method of claim 13, wherein said step of observing the luminescent emission comprises placing a filter intermediate the tooth and an eye of an observer, and observing the luminescent emission through the filter.

16. The method of claim 15, wherein said filter comprises a high-pass filter having a cutoff wavelength in the green region of the visible spectrum.

17. The method of claim 13, further comprising:

identifying the dentin layer of the tooth, the dentin layer comprising a luminescent region outside the dark outer ring, the dentin layer being less intensely luminescent than the intensely luminescent region, whereby the dentin layer appears yellow-green.

18. The method of claim 17, further comprising:

identifying the enamel layer of the tooth, the enamel layer comprising an area beyond the luminescent region comprising the dentin layer of the tooth, the enamel layer being less luminescent than the dentin layer.

19. The method of claim 13, wherein said desired wavelength comprises 405 nm.

20. A method of excavating carious material in a tooth, comprising:

providing a dental handpiece having a housing, and a drill head protruding from the housing, the drill head being operably connected to a motor mounted in the housing, the dental handpiece further including a light source mounted in the housing and being operable to produce a light through an opening in the housing, the opening being located in the housing such that the light produced by the light source is projected substantially in a direction along which the drill head protrudes from the housing, said light having a desired wavelength operable to produce tooth luminescence;

activating the light source to produce said light;

positioning the dental handpiece to project said light onto the tooth, said light causing a luminescence of the tooth;

observing the luminescence of the tooth and thereby identifying the carious material;

actuating the drill head; and applying the drill head to the carious material.

21. The method of claim 20, wherein said desired wavelength comprises 405 nm.

22. The method of claim 20, wherein said step of observing the luminescence of the tooth and thereby identifying the carious material comprises the steps of:

identifying a red-orange central region surrounded by an intensely luminescent yellow-green region and a dark outer ring, whereby the intensely luminescent region is intermediate the red-orange central region and the dark outer ring; and recognizing the red-orange central region as a bacterially invaded zone.

23. The method of claim 22, wherein said step of observing the luminescence of the tooth and thereby identifying the carious material further comprises the steps of:

placing a filter intermediate the tooth and an eye of an observer; and observing the luminescence of the tooth through the filter.

24. The method of claim 22, further comprising:

identifying a dentin layer of the tooth, the dentin layer comprising a luminescent region outside the dark outer ring, the dentin layer being less intensely luminescent than the intensely luminescent region, whereby the dentin layer appears yellow-green.

25. The method of claim 24, further comprising:

identifying an enamel layer of the tooth, the enamel layer comprising an area beyond the luminescent region comprising the dentin layer of the tooth, the enamel layer being less luminescent than the dentin layer.

26. A method of excavating carious material in a tooth, comprising:

providing a dental handpiece having: a housing; excavation means for excavating a portion of carious material occupying a portion of the tooth, said excavation means integral with said dental handpiece; illumination means for emitting a light of a desired wavelength operable to produce tooth luminescence, said illumination means mounted in said housing; and guide means for guiding an emitted light from said illumination means to an opening in said housing, said opening being located in said housing such that said emitted light is projected onto said tooth when said excavation means is operably positioned for excavating said portion of carious material;

activating the illumination means to produce said light;

positioning the dental handpiece to project said light onto the tooth, said light causing a luminescence of the tooth;

observing the luminescence of the tooth and thereby identifying the carious material;

actuating the excavation means; and applying the excavation means to the carious material.

27. The method of claim 26, wherein said step of observing the luminescence of the tooth and thereby identifying the carious material comprises the steps of:

identifying a red-orange central region surrounded by an intensely luminescent yellow-green region and a dark outer ring, whereby the intensely luminescent region is intermediate the red-orange central region and the dark outer ring; and recognizing the red-orange central region as a bacterially invaded zone.

28. The method of claim 27, wherein said step of observing the luminescence of the tooth and thereby identifying the carious material further comprises the steps of:

placing a filter intermediate the tooth and an eye of an observer; and observing the luminescence of the tooth through the filter.

* * * * *